United States Patent
Van Der Lelie et al.

(10) Patent No.: US 6,472,152 B1
(45) Date of Patent: Oct. 29, 2002

(54) DIAGNOSTIC SYSTEMS AND METHOD FOR DETERMINING THE PRESENCE OF A GENOTOXIC AND/OR TOXIC COMPOUND IN A SAMPLE

(75) Inventors: Daniel Van Der Lelie, Mol; Luc Agnes Louis Jean Bosco Regniers, Dessel; Safiyh Taghavi, Liege; Philippe Gilbert Ghislain Corbisier, Mol; Luc Philippine Edouard Verschaeve, Brussels, all of (BE)

(73) Assignee: Vlaamse Instelling Voor Technologish Onderzoek (VITO), Mol (BE)

(*) Notice: Subject to any disclaimer, the term of this patent is extended or adjusted under 35 U.S.C. 154(b) by 0 days.

(21) Appl. No.: 09/424,031
(22) PCT Filed: Apr. 12, 1999
(86) PCT No.: PCT/BE99/00049
§ 371 (c)(1), (2), (4) Date: Jan. 27, 2000
(87) PCT Pub. No.: WO99/53092
PCT Pub. Date: Oct. 21, 1999

(30) Foreign Application Priority Data
Apr. 14, 1998 (EP) .......... 98870081

(51) Int. Cl.⁷ .......... C12Q 1/68; C12Q 1/00; C12N 1/20
(52) U.S. Cl. .......... 435/6; 435/4; 435/8; 435/252.3; 435/252.33
(58) Field of Search .......... 435/4, 6, 8, 252.3, 435/252.33

(56) References Cited

FOREIGN PATENT DOCUMENTS

| EP | 0 649 905 | 4/1995 |
|---|---|---|
| EP | 0 673 439 | 9/1995 |
| WO | WO92/15687 | 9/1992 |
| WO | WO94/01584 | 1/1994 |
| WO | WO94/13831 | 6/1994 |
| WO | WO96/16187 | 5/1996 |
| WO | WO97/41251 | 11/1997 |

OTHER PUBLICATIONS

Belkin et al. A panel of stress–responsive luminous bacteria for the detection of selected classes of toxicants. Wat. Res. 1997, vol. 31, pp. 3009–3016.*

Gilbert et al. Measurement of in vivo expression of nrdA and nrdB genes of *Escherishia coli* by using lacZ gene fusions. Mol. Gen. Genet. 1990, vol. 220 pp. 400–408.*

Van Der Lelie et al., "The use of biosensors for environmental monitoring," *Research In Microbiology*, vol. 145, pp. 67–74 (1994).

Belkin et al., "A panel of stress–responsive luminous bacteria for the detection od selected classes of toxicants," *Water Research*, vol. 31, No. 12, pp.3009–3016, (1997).

Rupani et al., "On–line monitoring of recombinant *Escherichia coli* in batch and cotinuous cultures using a grpE promoter bioluminescence reporter gene system," *Abstracts Papers of the American Chemical Society*, vol. 207 (1994).

Orser et al., "Use of prokaryotic stress promoters as indications of the mechanisms of chemical toxicity" *In Vivo Toxicology*, vol. 8. No. 1, pp. 71–85 (1995).

International Search Report for application No. PCT/BE99/00049 dated Jun. 29, 1999.

* cited by examiner

*Primary Examiner*—Remy Yucel
*Assistant Examiner*—Konstantina Katcheves
(74) *Attorney, Agent, or Firm*—Merchant & Gould P.C.

(57) ABSTRACT

This invention concerns a diagnostic system made of: a transformed microorganism capable of an increased reporter activity upon exposure to an environmental insult, said microorganism having a stress inducible promoter sequence being operatively linked to a reported encoding nucleic acid sequence encoding a reporter molecule resulting in a signal that can be assayed, and of a transformed microorganism having a constitutive and non stress inducible promoter sequence being operatively linked to a reporter encoding nucleic acid sequence encoding a reporter molecule resulting in a signal that can be assayed.

10 Claims, 5 Drawing Sheets

DIAGNOSTIC SYSTEMS AND METHOD FOR DETERMINING THE PRESENCE OF A GENOTOXIC AND/OR TOXIC COMPOUND IN A SAMPLE

FIELD OF THE INVENTION

The present invention is related to a diagnostic system and to a method for determining the presence of a genotoxic compound in a sample.

BACKGROUND OF THE INVENTION AND STATE OF THE ART

The International Patent Application PCT/EP96/01745 describes a recombinant nucleic acid sequence, a host micro-organism comprising said nucleic acid sequence and the use of said host micro-organism for detecting the presence of genotoxic compounds in a sample. Said bacterial genotoxicity test is based on bioluminescence and allows an easy, very rapid and low cost detection of genotoxic compounds. The test was shown to be at least as sensitive as the Ames test and SOS-chromotest and to allow genotoxicity kinetics measurements as well as a simultaneous evaluation of the toxicity of the test compound or -material (van der Lelie et al., 1997). This new test, referred to as the VITOTOX® test was therefore considered to be a valuable short-term genotoxicity and toxicity test for many different purposes.

The test is based on bacteria that contain the lux operon of *Vibrio fischeri* under transcriptional control of the recN gene, that is part of the SOS-system. After incubation of the bacteria in the presence of a genotoxic compound, the recN promoter is derepressed, resulting in expression of the lux operon. This expression results in light production in function of genotoxicity. Originally, the test was performed with different modified *Escherichia coli* and *Salmonella typhimurium* strains. *Salmonella typhimurium* strains (TA98, TA100 and TA104) were further used, as the bacteria are well known for mutagenicity testing and because the same bacteria could also be used for a classical Ames test, should this be required. The construct using a recN promoter up mutation (recN 2-4) gave the best results in all strains. Furthermore, as all Salmonella strains gave very comparable results, it has been proposed to further use only the TA104 constructs [called TA104 (recN2-4)] as it was shown to be sometimes a little more sensitive than the other hybrid strains (van der Lelie et al., 1997).

However, some compounds act directly on the light production (e.g. aldehydes, organic solvents) or enhance the metabolism of the bacteria creating false-positive results.

AIMS OF THE INVENTION

The present invention aims to provide a new diagnostic system and method for the detection of environmental insults such as the presence of a genotoxic compound into a sample, which do not present the drawbacks of the state of the art.

A main aim of the present invention is to provide a new diagnostic system and method which will exclude false-positive and false-negative results.

A further aim of the present invention is to provide such a diagnostic system and method which could be used for the screening of genotoxic compounds obtained in the chemical, cosmetical or pharmaceutical industry field, as a prevalidation study of intermediate or active chemical, cosmetical and/or pharmaceutical compounds.

A last aim of the present invention is to provide such a diagnostic system and method which allow an automatic screening upon very small volume of sample.

DESCRIPTION OF THE INVENTION

The present invention is related to a diagnostic system made of a transformed micro-organism capable of an increased reporter activity upon exposure to an environmental insult, preferably exposure to a genotoxic compound, said micro-organism having a stress inducible promoter sequence, preferably a promoter sequence which is inducible by a genotoxic compound, said promoter sequence being operatively linked to a reporter encoding nucleic acid sequence encoding a reporter molecule resulting in a signal that can be assayed, and of a transformed micro-organism having a constitutive and non-stress inducible promoter sequence, preferably a constitutive promoter sequence which is not inducible by said genotoxic compound, said promoter sequence being operatively linked to a reporter encoding nucleic acid sequence encoding a reporter molecule resulting in a signal that can be assayed.

Preferably, both transformed micro-organisms are bioluminescent micro-organisms and the signal can be assayed as light production. Other possibilities are the peroxydase, alkaline phosphatase, β-gal and gus genetic sequence, where the signal will be assayed as a colorimetric modification or a chemiluminescent light production by using a colorimetry analyser or a photomultiplier device.

Advantageously, the diagnostic system according to the invention is made of two transformed bioluminescent micro-organisms, the first bioluminescent micro-organism is "activated" in the presence of a genotoxic compound and results in a signal that can be assayed as light production, while the light production of the second bioluminescent micro-organism is not influenced by the presence of a genotoxic compound in the sample.

Nucleic acid sequence encoding a reporter resulting in a signal that can be assayed as light production has been already described in the state of the art. Preferably, the transformed bioluminescent micro-organisms according to the invention comprise luciferase A and B genes, also identified as expressive lux genes complex, comprising the luxA and luxB genes or a translational luxAB fusion gene. The transformed bioluminescent micro-organisms may also comprise the luciferase C, D and E genes, required for production of limiting fatty acid substrate that is used in recycling.

According to a preferred embodiment of the present invention, the diagnostic system comprises a transformed bioluminescent micro-organism having a constitutive and non stress inducible promoter sequence with a Sigma 70 consensus sequence (TTGACA(−35) . . . 17/18 bp . . . TATAAT(−10)) and whose transcription is not regulated positively or negatively at the promoter level. Said promoter consensus is described in Hoopes B C and McClure W R (1987): Strategies in Regulation of Transcriptional Initiation; in "*Escherichia Coli* and *Salmonella typhimurium*, Cellular and Molecular Biology, FC Neidhart, J L Ingraham, K B Low, B Maganasik, M Schaechter, H E Umbaeger (eds.), American Society for Microbiology, Washington D.C., pp 1231–1240.

According to a preferred embodiment of the present invention, the transformed bioluminescent micro-organisms are selected from the group consisting of *E. coli* or *Salmonella typhimurium,* and are advantageously suitable Ames test micro-organism(s), preferably selected from the group consisting of TA98, TA100, TA102, TA104, TA1535, TA1538, TA7001 to TA7006, and TA7041 to TA7046, and/or having the micro-organism deposit number LMG P-18318. The micro-organism with deposit number LMG P-18318 will be identified hereafter as the "pr1" strain.

Advantageously, the stress inducible promoter sequence in the transformed bioluminescent micro-organism of the diagnostic system according to the invention is selected from the group consisting of groEL, dnaK, grpE, phoA, glnA, lon, lysU, rpoD, clpB, clpP, uspA, katG, uvrA, frda, micF, fabA, lac, his, sodA, sodB, soi-28, recA, xthA, narG, recF, recj, recN, recO, recQ, ruv, uvrD, ars, cad, mer, pco, and sfiA.

According to a preferred embodiment of the present invention, the stress inducible promoter sequence is recN, advantageously recN2-4. Said micro-organism will be identified hereafter as the "recN2-4" strain In a preferred embodiment, the diagnostic system according to the invention comprises a transformed bioluminescent micro-organism having a stress inducible promoter sequence being a SOS regulator promoter sequence, having preferably an induction ration higher than 40, and comprising advantageously a mutation improving the promoter strength or regulation, said mutation not destroying the SOS regulation.

A specific example of mutated recN promoter sequence is described in the International Patent Application PCT/EP96/01745, incorporated hereafter by reference.

Said stress inducible promoter sequence comprises also a promoter up-mutation, preferably a promoter up-mutation in the −35 region of said promoter, described in the International Patent Application PCT/EP96/01745, incorporated hereafter by reference.

The present invention is also related to a diagnostic kit comprising the elements of the diagnostic system according to the invention and possibly the necessary additional reactants, diluants and/or solid supports for said diagnostic such as a buffer solution, a solution comprising a specific marker such as the X-gal (5-bromo-4-chloro-3-indoyl-β-galactoside) for a diagnostic based upon the use of a β-gal genetic sequence, the luminol for a diagnostic based upon the use of a peroxydase genetic sequence, etc . . .

The present invention is also related to a general method for the diagnostic of an environmental stress or insult, preferably for determining the presence of a genotoxic compound in a sample. Said method comprises the steps of exposing the diagnostic system according to the invention to said environmental insult (preferably comprising the steps of exposing the diagnostic system to the genotoxic compound present in the sample) and measuring a signal, preferably a change in luminescence of said diagnostic system.

The present invention is also related to a method for determining the kinetics of genotoxicity of a compound into a sample, based upon the above-identified method, wherein the measuring of luminescence of both inducible and constitutive transformed micro-organisms occurs at multiple points in time, preferably continuously, and in addition carrying out the step of determining the signal-to-noise (S/N) ratio for the transformed micro-organisms at said point and time, dividing the S/N ratio of the inducible micro-organism by that of the constitutive micro-organisms and plotting these data, said plotting representing the corrected kinetics of genotoxicity of the genotoxic compound in the sample.

Advantageously, the diagnostic system and method according to the invention can be combined with the Ames and/or SOS chromotest(s) and method(s), as described hereafter.

The present invention is also related to an analysis method of an environmental insult, comprising the steps of:
performing the diagnostic of said environmental insult as above described,
calculating the signal to noise ratio of both the transformed micro-organisms,
classifying said environmental insult as toxic if at least one of the calculated signal to noise ratios is lower than 0.8,
classifying said environmental insult as having no effect if the signal to noise ratio of the micro-organism comprising the stress-inducible promoter sequence lies between 0.8 and 1.2, and
classifying said environmental insult as inducing and genotoxic if the signal to noise ratio of the micro-organism comprising the stress-inducible promoter sequence is higher than 1.2 and is at least 50% higher than the signal to noise ratio of the micro-organism comprising the constitutive promoter sequence.

The present invention is also related to an installation for determining if a compound in a sample is genotoxic and/or toxic, comprising a diagnostic system as above described induced by said sample, a detection system comprising a detection apparatus able to assay the signal from said diagnostic system, said detection system being connected to a computer programmed to carry out the analysis method as above described.

The present invention will be described in detailed in the non-limiting following examples, in reference to the following figures.

DETAILED DESCRIPTION OF THE INVENTION

Materials and Methods
Ames Test and SOS Chromotest

The SOS chromotest and the Ames test are well known and widely used bacterial genotoxicity tests (e.g., Quillardet & Hofnung, 1993; Mersch-Sundermann et al., 1994; Mortelmans et al., 1986). The "classical" Ames test was routinely performed with *Salmonella typhimurium* strains TA98 and TA100 using the standard protocol described by Maron and Ames (1983). The SOS-chromotest was purchased as a test kit from Orgenics ltd (Yavne, Israel). The test was performed as indicated in the manufacturers instructions.
The VITOTOX® Test
*Salmonella typhimurium* Strains The recN promotor region, that was part of the *E. coli* recN gene (Rostas et al., 1987) contains two LexA binding sites. One LexA binding site overlaps with the −35 region while the second overlaps with the −10 region and the transcription start point of the recN promoter. The *E. coli* recN promoter was cloned upstream of the luxCDABE operon of the expression vector pMOL877 (van der Lelie et al., 1997). This resulted in pMOL1066. Since the recN promoter is under control of the bacterial SOS system, the expression of the lux operon became SOS regulated. This results in light production in the presence of genotoxins. Some recN promoter derivatives were also cloned in pMOL877. One lacking the LexA2 site resulted in pMOL1067, one having a promoter up mutation (pMOL1068) and one being a combination of both (pMOL1069). All constructs were introduced in the Ames test strains TA98, TA100 and TA104 and were able to detect genotoxic compounds. However, as the best results were obtained with strain TA104 (pMOL1068) this strain was further used in the so-called VITOTOX® test. It was extensively described before and was designated as TA104 recN2-4 as it contains the recN2-4 PCR fragment (van der Lelie et al., 1997). Besides TA104 recN2-4 (the tester strain) the so-called TA104 pr1 strain is now added as a "control strain". Plasmid pMOL1046 was constructed by cloning at random EcoRI digested DNA fragments from *Alcaligenes eutrophus* CH34 in the luxCDABE-expression vector (pMOL877). *A. eutrophus* CH34 (ATCC 43123) is a gram-negative non-pathogenic soil bacterium derived from a decantation tank of a zinc factory (Mergeay et al., 1985, J.Bact). After transformation into *E. coli* 1106 (Murray et al., 1977, Mol. Gen.Genet.), clones were selected for light production. The best constitutively light emitting clone, giving the highest light production as quantified in a luminometer, was then selected out of the different plasmid transformants (=plasmid pMOL1046) and introduced into the *S. typhimurium* strain TA104. This was named the "pr1" strain. It contains luxCDABE-genes under control of a constitutive promoter so that the light production is not influenced by genotoxic compounds. The pr1 strain is used in parallel with the recN2-4 strain and cultivated and treated in exactly the same way.

Test Procedure

1. Cultures

Bacteria were incubated overnight on a rotative shaker at 37° C. in 869 medium; this is a normal growth medium equivalent to Luria Broth medium supplemented with extra $CaCl_2$ to allow optimal bacterial growth and is described in van der Lelie et al. (1997, Mutation Res.). The next morning the bacterial suspension was diluted 10 times in 869 medium and 50 µl of the dilution was then inoculated in 2.5 ml of 869 medium and incubated for one more hour at 37° C. on a rotative shaker (170 rpm).

2. Preparation of the 96-well Plates

In the meantime 96-well plates were prepared so as to contain 10 µl of either the solvent, different concentrations of the test compound or the positive control for genotoxicity testing with (2-AF) or without (4-NQO) S9-mix. The S9 mixture, prepared according to Maron and Ames (1983, Mutation Res.), is used to detect the presence of compounds that only become genotoxic after metabolic activation. The S9-mix was prepared freshly before use. For tests with S9-mix, 140 µl of the bacteria (recN2-4 or pr1) was added to 860 µl poor 869 medium and 400 µl S9-mix. From this mixture 90 µl was then added to the 10 µl solution already present in the wells. For tests without S9-mix, 1260 µl of poor 869 medium was added to 140 µl of the bacterial suspension and 90 µl of the mixture was then transferred to wells containing 10 µl of the test compound or controls.

3. Genotoxicity and Toxicity Measurements

A 96-well microplate luminometer (Luminoscan from Berthold) was used for the measurements of the light production following exposure to the test compounds. Light emission from each of the wells was measured every 5 minutes during 5 hours (30° C., 1sec/well, 60 cycles of 300 sec each). After completing the measurements, the data were transferred into an MS Excel macro sheet and the signal-to-noise ratio (S/N), being the light production of exposed cells divided by the light production of non-exposed cells, was calculated for each measurement. A compound was considered genotoxic when the S/N was higher than 2 for at least two concentrations and when a clear dose-effect relationship was observed. In the second experiment in which the TA104 pr1 strain was introduced, the S/N was calculated for the RecN2-4 and pr1 strains separately as well as the ratio between the maximum and mean S/N values of the recN2-4 and pr1 strains (rec/pr1). All calculations were performed between 60 and 240 minutes of incubation. Here, a compound is considered genotoxic when the S/N in the recN2-4 strain is greater than1.5× the solvent control value (and not "2" as was initially done), but only when this increase is not accompanied by a comparable increase in the pri strain (that would indicate a non-genotoxic induction mechanism). A compound is genotoxic when the S/N ratio's of the recN2-4 over the pr1 strain is equal or higher than 1.5 (limit set on experimental grounds). In this way "false positive" results can be avoided.

"False negative" results can be identified when the S/N ratio of the recN2-4 strain remains between 0.8 and 1.2, whereas the S/N ratio of the pr1 sensor decreases below 0.8. This is typically the case for samples being genotoxic as well as toxic at the same time.

The pr1 strain is furthermore also very valuable for toxicity evaluation. Bacterial toxicity is assumed when the light emission is substantially decreasing in a dose-dependent way and attains S/N values lower than 0.8 within the first 30 minutes of the test.

Figure 5:
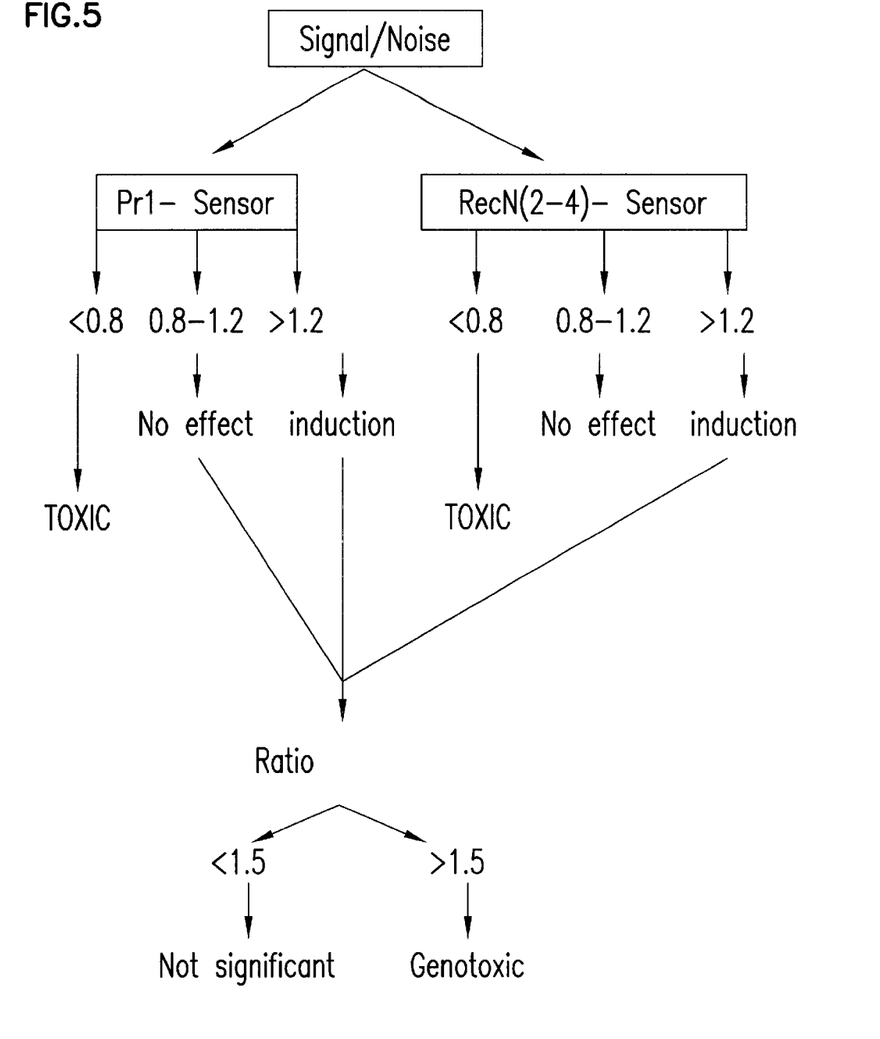
FIG. 5 represents a determination chart to differentiate the possible outcomes of a diagnostic test according to the invention.
Figure 6:
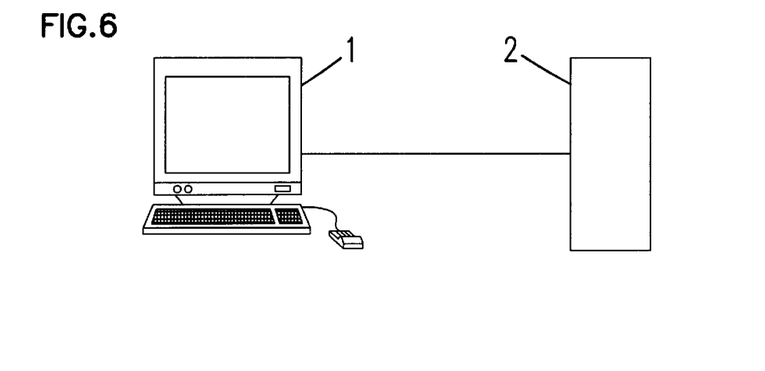
FIG. 6 represents an installation according to the invention.

Automatisation of the system is possible, using an installation as described in FIG. 6. An detection apparatus (2) comprising at least a detector for the signal that is emitted from a diagnostic system as above described, is linked to a computer (1) which receives and processes the detector data according to the analysis method as above described and as clarified in FIG. 5. This way, an automised analysis of samples and classification as toxic and/or genotoxic is possible.

Test Compounds

A number of commercially available well known compounds that were evaluated before with the TA104 recN2-4 strain alone (see van der Lelie et al., 1997) were re-evaluated in the present work using the TA104 recN2-4 and TA104 pr1 strain. They are given in table 1.

TABLE 1

VITOTOX test results for selected chemicals

| COMPOUND* | S9** | DOSE RANGE TESTED | S/R > 2 (recN2 – 4) | concentration at which S/R's of rec/pri >1.5 MAX | concentration at which S/R's of rec/pri >1.5 MEAN | Toxic (pri) |
|---|---|---|---|---|---|---|
| Furazolidone | — | 0.125–32 ppb | 0.25 ppb | 0.5 ppb | 0.25 ppb | – |
| 4NQO | — | 0.4–102 ppb | 0.8 ppb | 1.6 ppb | 0.8 ppb | – |
| Nifuroxazide | — | 2–256 ppb | 8 ppb | 16 ppb | 8 ppb | + |
| MMC | — | 3.9–500 ppb | 31.2 ppb | 31.2 ppb | 15.6 ppb | – |
| 3-Nitrofluoranthene | — | 7.9–1000 ppb | 15.7 ppb | 31.3 ppb | 15.7 ppb | – |
| 3-Nitrofluoranthene | +25 | 7.9–1000 ppb | 15.7 ppb | 31.2 ppb | 15.7 ppb | – |
| Nifuroxazide | — | 0.04–5.12 ppm | 0.04 ppm | 0.04 ppm | 0.04 ppm | + |
| 3Nitrofluoranthene | — | 0.004–0.512 ppm | 0.032 ppm | 0.064 ppm | 0.032 ppm | – |
| Carbadox | — | 0.04–5.12 ppm | 0.08 ppm | 0.08 ppm | 0.04 ppm | – |
| Nalidixic acid | — | 0.02–2.56 ppm | 0.16 ppm | 0.16 ppm | 0.16 ppm | + |
| 2,4,5,7Tetranitro-9-fluorenone | — | 0.01–1.28 ppm | 0.08 ppm | 0.16 ppm | 0.04 ppm | + |
| B(a)P | +25 | 0.025–6.4 ppm | 0.2 ppm | 0.2 ppm | 0.1 pm | – |
| 2AF | +25 | 0.2–3.2 ppm | 0.2 ppm | 0.2 ppm | 0.2 ppm | – |
| B(a)P | +25 | 0.1–1.6 ppm | 0.2 ppm | 0.2 pm | 0.2 pm | – |
| 2,7Dinitrofluoreen | +25 | 0.04–10 ppm | 0.62 ppm | 0.62 ppm | 0.62 ppm | – |
| B(a)P | +100 | 0.1–12.8 ppm | 0.8 ppm | 0.8 ppm | 0.4 ppm | – |
| ICR 191 Acridine | — | 0.02–2.5 ppm | 0.62 ppm | 1.25 ppm | 0.31 ppm | – |
| a-Naphtylamine | +25 | 0.08–10 ppm | 5 ppm | 2.5 ppm | 2.5 ppm | – |
| 4Nitro-o-Phenylenediamine | — | 0.79–100 ppm | 3.1 ppm | 3.1 ppm | 1.57 ppm | + |
| Fluoranthene | +100 | 3.1–400 ppm | 3.1 ppm | 3.1 ppm | 3.1 ppm | – |
| H2O2 | — | 0.25–32 ppm | 2 ppm | 4 ppm | 2 ppm | + |
| K2Cr2O7 | — | 0.5–64 ppm | 4 ppm | 4 ppm | 4 ppm | + |
| Phenanthrene | +100 | 3.1–400 ppm | 6.2 ppm | 6.2 ppm | 6.2 ppm | + |
| MMS | — | 4–64 ppm | 16 ppm | 8 ppm | 8 ppm | – |
| MMS | — | 0.5–128 ppm | 8 ppm | 8 ppm | 8 ppm | – |
| Chrysene | +100 | 0.15–20 ppm | — | 10 ppm | 5 ppm | – |
| 4Nitro-o-Phenylenediamine | +25 | 0.79–100 ppm | 12.5 ppm | 12.5 ppm | 12.5 ppm | + |
| N-Nitrosodiethylamine | +25 | 3.25–480 ppm | 120 ppm | 120 ppm | 240 ppm | – |
| Epichlorohydrine | — | 4–512 ppm | 120 ppm | 256 ppm | 120 ppm | – |
| EMS | — | 8–1024 ppm | 256 ppm | 256 ppm | 256 ppm | – |
| Epichlorohydrine | — | 8–1024 ppm | 256 ppm | 512 ppm | 128 ppm | + |
| ZnCl2 | — | 0.5–64 ppm | — | — | — | + |
| CdCl2 | — | 0.78–100 ppm | — | — | — | + |
| Coumermycine A1 | — | 1.56–200 ppm | — | — | — | + |
| Sodium azide (NaN$_3$) | — | 2–256 ppm | — | — | — | + |
| 2,7Dinitrofluoreen | — | 0.04–10 ppm | — | — | — | – |
| a-Naphtylamine | — | 0.08–10 ppm | — | — | — | – |

*some chemicals were investigated several times in different dose-ranges or conditions;
**μl/ml of S9-mix used at incubation Results Earlier reported results with the VITOTOX®-test were obtained in *Salmonella typhimurium* strain TA104 RecN2-4 (van der Lelie et al., 1997). In order to further improve the test we introduced the pr1 strain. Results obtained in the RecN2-4 strain should be evaluated in comparison with the results obtained in the pr1 strain where an increased light production cannot be due to a genotoxic event. An increased light production in the recN2-4 strain can therefore only be interpreted as an indication of genotoxicity when this is not accompanied by a comparable increase in light production in the pr1 strain.

Figure 1:
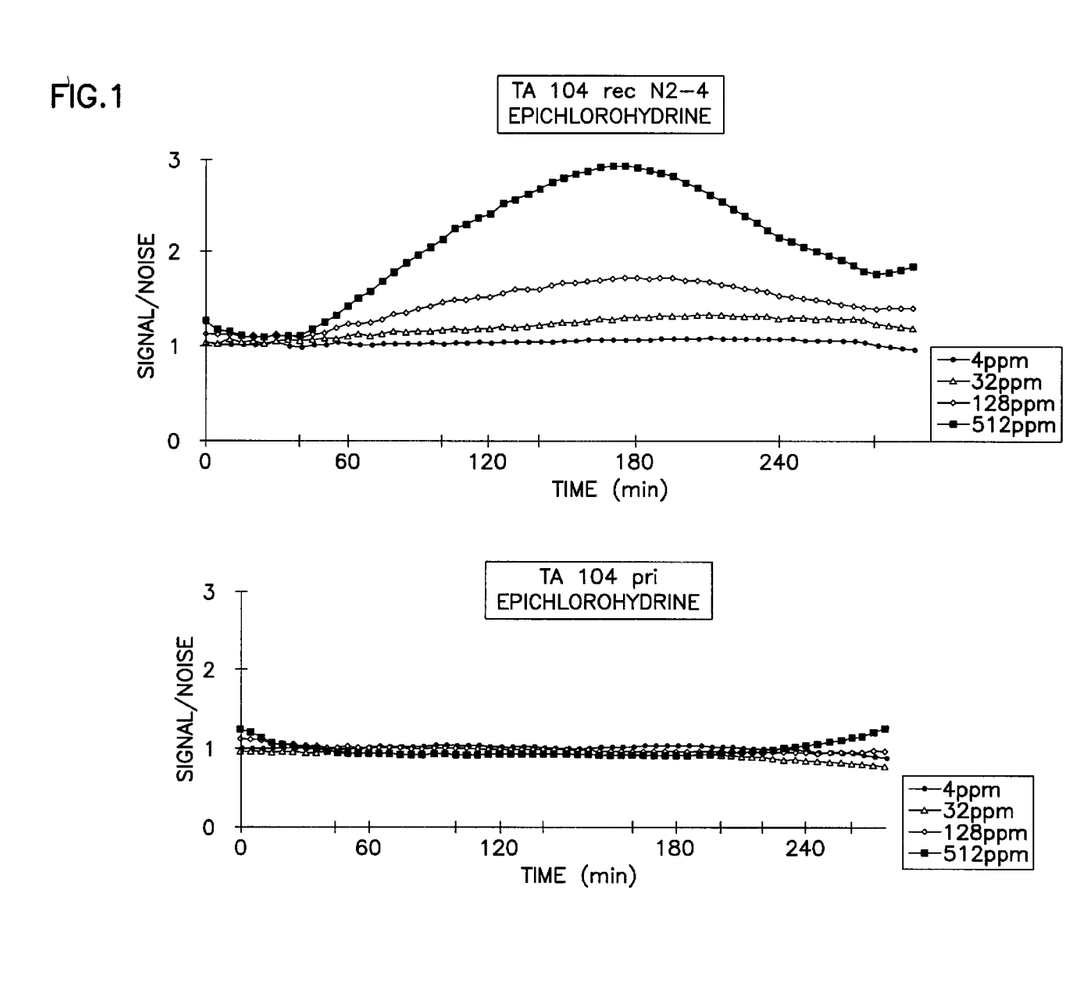
FIG. 1 represents signal-to-noise ratio for epichlorohydrine in the recN2-4 and pr1 strains.
Figure 2:
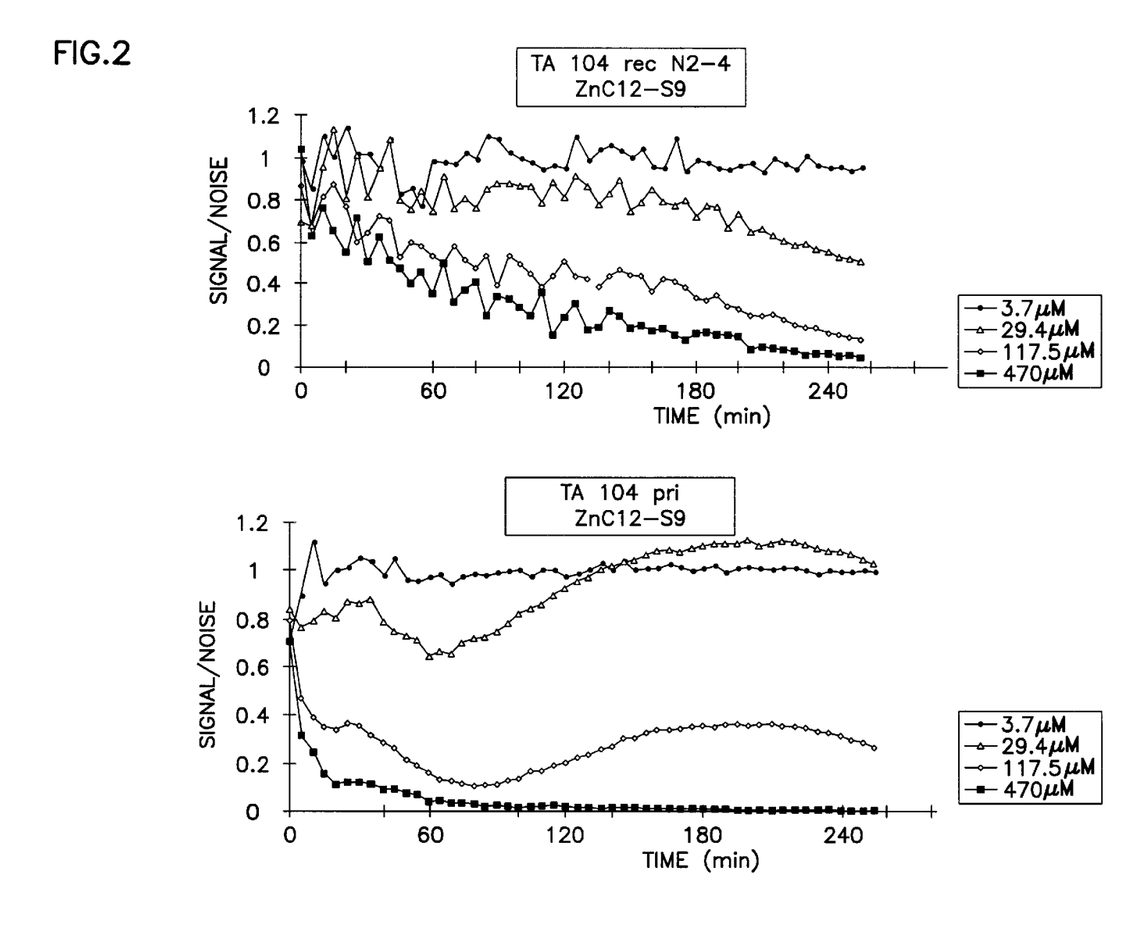
FIG. 2 represents signal-to-noise ratio for $ZnCl_2$ in the recN2-4 and pr1 strains.
Figure 3:
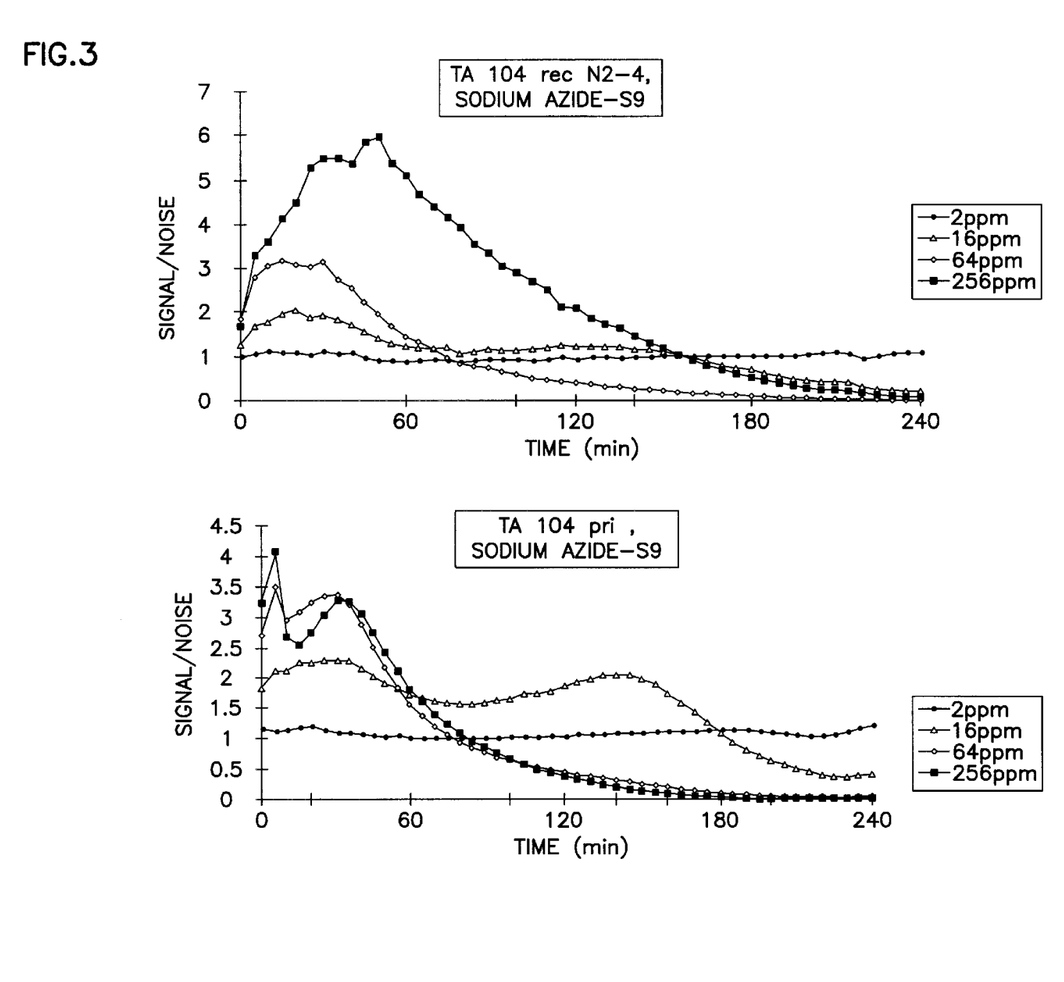
FIG. 3 represents signal-to-noise ratio for sodium azide in the recN2-4 and pr1 strains.
Figure 4:
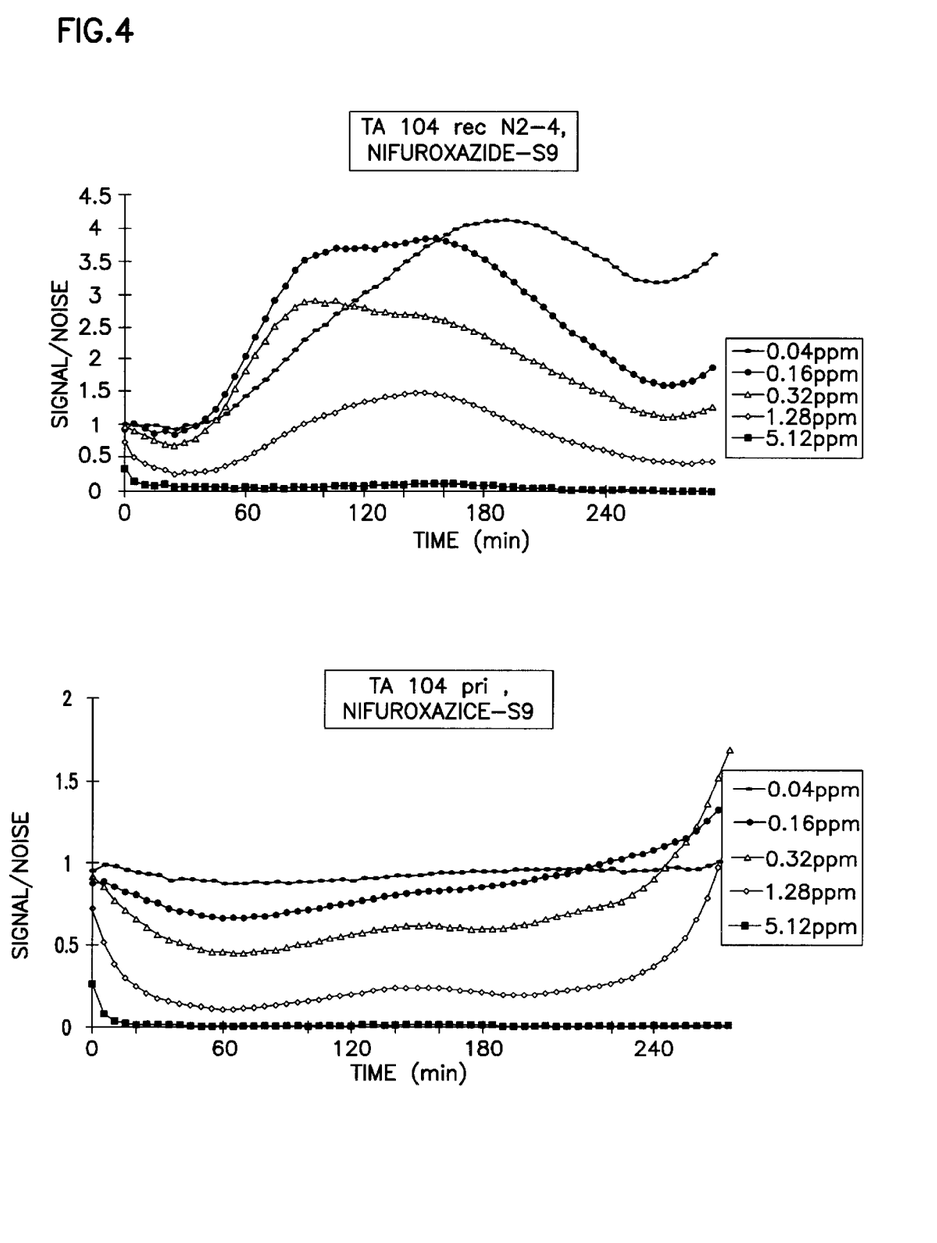
FIG. 4 represents signal-to-noise ratio for nifuroxazide in the recN2-4 and pr1 strains.

Using both bacterial strains we re-evaluated a number of the earlier studied chemicals. The results are given in table 1. The table gives the concentrations at which the maximal S/N value in the recN2-4 tester strain becomes ≧2, as well as the concentrations where the ratio between the maximal and mean recN2-4 S/N and pr1 S/N reaches 1.5 or more (rec/pr1). Finally the table also indicates the presence of toxicity within the dose-range tested and as evaluated by the pr1 S/N curves. It can be seen that known genotoxic compounds were indeed evaluated as genotoxic whereas non-genotoxic compounds did not show the required S/N ratio's in the given dose-ranges. A few examples of the results were graphically represented in FIGS. 1–4 (examples of tests without S9mix). FIG. 1 gives the S/N curves for epichlorohydrine in the recN2-4 and pr1 strains. In the recN2-4 strain the S/N values became greater than 2 at the dose of 256 ppm, whereas S/N values in the pr1 strain did not greatly deflect from 1. FIG. 2 gives the results for ZnCl$_2$ that is non-genotoxic but toxic for *Salmonella typhimurium* TA104 at concentrations higher than 7.4 μM. Sodium azide is given as a third example in FIG. 3. Here the S/N ratio was considerably greater than 2 in both the recN2-4 and pr1 strains and indications of toxicity are obtained with time (S/N<0.8). FIG. 4 illustrates the results that were obtained for nifuroxazide. Referring to the recN2-4 strain lower doses were apparently more genotoxic than higher doses but the pr1 strain showed a dose-dependent decrease in light production indicating toxicity.

Discussion

The VITOTOX®-test is a sensitive and rapid method to detect genotoxic compounds (van der Lelie et al., 1997). However, if only the recN2-4 strain is used (as was initially done) some misinterpretations were possible. The present invention is based upon the use of the pr1 strain. The added value of the pr1 strain was illustrated by a few examples. In FIG. 1 an example is given of a genotoxic compound (epichlorohydrine) that was not toxic in the given dose-range. Based on the results obtained from the recN2-4 strain alone one may conclude that the compound was genotoxic as a dose-dependent increase in light production was observed that exdeeded the "noise" value by more than a factor of two (S/N>2). Inclusion of the pr1 strain only confirmed this evaluation. If an increased light production was found in the pr1 strain we indeed should conclude that this was due to another induction mechanism than genotoxicity (e.g., increased cell proliferation which would enhance the "noise level" compared to that of unexposed cultures, etc.). But this was not the case. There as also no sign of toxicity as there was no decreased light production. This was clearly the case for $ZnCl_2$ as indicated by the curves of FIG. 2. The figure for the recN2-4 strain shows that the dose of 3.7 $\mu$M is neither genotoxic nor toxic but at higher doses a decreased light emission is observed indicating a toxic effect followed by a certain recovery at the lower doses. This is confirmed by the pr1 strain where recovery is even more visible at doses up to 58.8 $\mu$M $ZnCl_2$. From 117.5 $\mu$M $ZnCl_2$ on, recovery is not possible anymore. $ZnCl_2$ was thus shown to be non genotoxic and only the lowest dose appeared to be devoid of any toxicity.

As indicated in the introduction and, materials and methods section the VITOTOX®-test is essentially based on detection of a SOS signal. It should therefore theoretically produce results that are more in agreement with the SOS chromotest than with the Ames test. Yet, some differences were previously found. The Inventors have reported for example a "positive" response for sodium azide while this compound normally scores "negative" in the SOS chromotest (van der Lelie et al, 1997). One reason for this discrepancy could be that the VITOTOX®-test uses the Ames-test's *Salmonella typhimurium* TA104 strain and therefore has the same characteristics, e.g., reduced DNA repair capability and increased permeability for complex molecules (as most pharmaceutical compounds). This is certainly a valid explanation in many instances but probably not for a small molecule like sodium azide ($N_3Na$). Here another reason for the difference with SOS chromotest results could be anticipated. It could for example be that the increased light production as found in the recN2-4 strain is due to another induction mechanism than genotoxicity. with the introduction of the pr1 strain one is able to verify this assumption. As can be seen from FIG. 3 the observed light production in the recN2-4 strain is not due to genotoxicity as increased light emission is also observed in the pr1 strain and this can not be due to a SOS response. Sodium azide should therefore be interpreted as non-genotoxic in our test. It is a good example of a "compound" that would be a "false positive" when only the recN2-4 strain was used.

The Inventors have tested and compared much more pharmaceutical compounds with the other bacterial tests. Results obtained by the different tests were most often completely in agreement with each other. The VITOTOX® test usually is also much more sensitive than the Ames or SOS chromotest as the minimal detectable concentrations are 1–100 times lower in the VITOTOX® test.

Another advantage of using the pr1 strain is that besides genotoxicity, toxicity can be better evaluated than with the recN2-4 strain alone. A genotoxic compound that is investigated at dose levels around the toxicity threshold can show S/N ratio's in the recN2-4 strain that are "intermediate" between genotoxicity and toxicity as increase in light production (due to genotoxicity) competes with a decrease (due to toxicity) resulting in a S/N ≈1. The compound would therefore be interpreted as neither genotoxic or toxic (false negative result). The pr1 strain will clearly show a decrease in the light emission indicating that the compound is already toxic at the given dose. This is, at least for some doses, illustrated in FIG. 4 where nifuroxazide was taken as an example. It can be seen that the lower doses gave the greatest genotoxic response because of dose-dependent toxicity. The S/N curves for the pr1 strain clearly indicates that only the lowest doses up to 0.16 ppm were not toxic. Higher doses may show toxicity combined with genotoxicity (e.g., 0.32 ppm) or may be too toxic to show genotoxicity (highest doses).

Both the recN2-4 and pr1 strains were shown to be able to detect toxic concentrations of a compound. However, the pr1 strain is more valuable in toxicity testing as S/N curves can not be influenced by genotoxicity and hence reflect only toxicity (or its absence). The pr1 strain apparently provides a perfect tool for those who are only interested in toxicity assessment. We are at present comparing toxicity assessment of chemicals and complex mixtures with the pr1 strain and with the Microtox®-test. The latter is one of the most currently used and internationally accepted microbial toxicity tests that is also based on bioluminescence (Hasting, 1978; Férard et al., 1983). According to the limited data already available to us the VITOTOX®-test gives the same results as the Microtox®-test but the former is more easy to perform and is often much more sensitive. The VITOTOX®-test, or only its pr1-element, may therefore also be considered as an extremely valuable toxicity test, at least when these preliminary results can be confirmed.

In conclusion it can be stressed that the TA104 recN2-4 and TA104 pr1 *Salmonella typhimurium* strains provide very valuable genotoxicity and/or toxicity testsystems. Both strains should be used concomitantly for genotoxicity testing whereas the pr1 strain is only required for toxicity testing. It was shown that the VITOTOX®-test provides a very rapid (within 2–4 hours), and very sensitive answer with regard to the (geno)toxicity of chemicals and that it may for that reason be very useful in screening and in pre-screening of new chemicals and intermediate products. As testing is performed in 96-well plates it is at least possible to investigate 8 chemicals (with and without addition of a metabolic enzyme fraction S9) per day or 40 chemicals per week. Measurements occur automatically and data collection and data handling can furthermore also almost completely be automated. Microplate robotisation should be able to multiply this rate with a factor of 10. Scale-up e.g. by increasing the amount of wells per plate is obvious. Labour costs are therefore maximally reduced.

Finally, a supplementary and very important asset is that only very small volumes of the test compound are required (less than 20 mg). This is particularly important for the pharmaceutical industry where only a few hundred milligrams of a compound are available in the discovery phase. It is just impossible to screen such new chemicals with (most) other test systems.

A deposit of the strain "pr1" was made on Apr. 1, 1998 according to the Budapest Treaty under the deposit number LMG P-18318 at the BCCM/LMG, Laboratorium voor Microbiologie—Bacteriënverzameling, Universiteit Gent, K. L. Ledeganckstraat 35, B-9000 Gent, Belgium.

REFERENCES

Férard J F, et al., (1983): Application d'un test d'inhibition de luminescence bacterienne de l'étude toxicologique d'effluents complexes et de substances chimique. Revue Francaise des Sciences de l'Eau 2: 221–237.

Hasting J W (1978): Bacterial bioluminescence: an overview. In: Methods in Enzymology. Academic Press, pp. 125–152.

Maron D M, Ames B N (1983): Revised methods for the Salmonella mutagenicity test. Mutation Res. 113: 173–215.

Mergeay M, et al., (1985): *Alcaligenes eutrophus* CH34 is a facultative chemolithotroph with plasmid-bound resistance to heavy metals. J. Bacteriology, 162, 328–334.

Mersch-Sundermann V, et al., (1994): SOS induction in *Escherichia coli* and Salmonella mutagenicity: a comparison using 300 compounds. Mutagenesis 9: 205–224.

Mortelmans K et al., (1986): Salmonella mutagenicity tests: II. Results from the testing of 270 chemicals. Environ. Molec. Mutagen. 8, suppl. 7: 1–119.

Murray N E, et al., (1977): Lambdoid phages that simplify the recovery of in vitro recombinants. Mol.Gen.Genet. 150: 53–61.

Quillardet P, Hofnung M (1993): The SOS chromotest: a review. Mutation Res. 297: 235–279.

Rostas K et al., (1987): Nucleotide sequence and LexA regulation of *Escherichia coli* recN gene. Nucl. Acids Res. 15: 5041–5049.

van der Lelie D et al., (1997): The VITO-TOX test, a SOS-bioluminescence *Salmonella typhimurium* test to measure genotoxicity kinetics. Mutation Res.389: 279–290.

van der Lelie D et al.,(1997): Two-component regulatory system involved in transcriptional control of heavy-metal homeostasis in *Alcaligenes eutrophus*. Molecular Microbiology 23 (3): 439–503.

What is claimed is:

1. A diagnostic system comprising:
   a first transformed micro-organism capable of an increased reporter activity upon exposure to an environmental insult, said micro-organism having a stress inducible promoter sequence being operatively linked to a nucleic acid sequence encoding a reporter molecule resulting in a signal that can be assayed, and
   a second transformed micro-organism having a constitutive and non-stress inducible promoter sequence being operatively linked to a nucleic acid sequence encoding a reporter molecule resulting in a signal that can be assayed,
   wherein said second and first microorganisms are *Salmonella typhimurium* microorganisms selected from the group consisting of Ames test micro-organism, micro-organism designated by deposit number LMG P-18318, transformed TA98, transformed TA100, transformed TA102, transformed TA104, transformed TA1538, transformed TA7001 to transformed TA7005, and transformed TA7041 to transformed TA7046, said micro-organisms being suitable to cooperatively detect said environmental insult while eliminating false positive and false negative result.

2. System according to claim 1, wherein the signals are assayed as light production and/or colorimetric modification.

3. System according to claim 1, wherein the stress inducible promoter sequence is selected from the group consisting of groEL, dnaK, grpE, phoA, glnA, lon, lysU, rpoD, clpB, clpP, uspA, katG, uvrA, frda, micF, fabA, lac, his, sodA, sodB, soi-28, recA, xtha, narG, recF, recJ, recN, recO, recQ, ruv, uvrD, ars, cad, mer, pco and sfiA.

4. System according to claim 1, wherein the constitutive and non stress inducible promoter sequence is a sequence with a Sigma 70 consensus sequence (TTGACA(−35) . . . 17/18 bp . . . TATAAT (−10)) and whose transcription is not regulated positively or negatively at the promoter level.

5. System according to claim 1 wherein the reporter encoding nucleic acid sequence comprises the luciferase A and B genes or a luxAB translation fusion gene.

6. System according to claim 1, wherein the reporter encoding nucleic acid sequence comprises the luciferase A and B genes and the luciferase C, D, and E genes.

7. System according to claim 1, wherein the environmental insult is the presence of a genotoxic and/or a toxic compound in a sample.

8. Diagnostic kit comprising the elements of the diagnostic system according to claim 1.

9. Method for the diagnostic of an environmental insult comprising the steps of:
   exposing the diagnostic system according to claim 1 to said environmental insult, and
   measuring a signal of the transformed micro-organism(s) of said diagnostic system.

10. The method according to claim 1, wherein the transformed micro-organism is bioluminescent.

* * * * *